United States Patent [19]

Inagaki et al.

[11] 4,412,951

[45] Nov. 1, 1983

[54] REAGENTS FOR MEASURING LIPASE ACTIVITY

[75] Inventors: Yoshio Inagaki; Masaki Okazaki; Shinsaku Fujita, all of Kanagawa, Japan

[73] Assignee: Fuji Photo Film Co., Ltd., Kanagawa, Japan

[21] Appl. No.: 316,025

[22] Filed: Oct. 28, 1981

[30] Foreign Application Priority Data

Oct. 28, 1980 [JP] Japan .................................. 55-151043

[51] Int. Cl.$^3$ ............................................ C07C 107/08
[52] U.S. Cl. ..................................... 260/202; 260/196; 260/201
[58] Field of Search ........................ 260/201, 196, 202

[56] References Cited

U.S. PATENT DOCUMENTS

| | | | |
|---|---|---|---|
| 2,155,493 | 4/1939 | Knight et al. ................. | 260/201 X |
| 2,888,452 | 5/1959 | Schmid et al. ................. | 260/202 X |
| 3,523,934 | 8/1970 | Haubrich ....................... | 260/201 X |
| 3,591,576 | 7/1971 | Haubrich ....................... | 260/201 X |
| 3,658,785 | 4/1972 | Ronco et al. ................... | 260/202 X |
| 4,058,515 | 11/1977 | Stingl et al. ................... | 260/201 X |
| 4,188,320 | 2/1980 | Kamachi et al. ............... | 260/196 X |
| 4,228,070 | 10/1980 | Milner et al. ................... | 260/202 X |
| 4,273,708 | 6/1981 | Kilminster et al. ............ | 260/202 X |

OTHER PUBLICATIONS

Lubs, The Chemistry of Synthetic Dyes and Pigments, Reinhold Publ. Corp. N.Y. pp. 670-671 (1955).

*Primary Examiner*—Helen M. S. Sneed
*Attorney, Agent, or Firm*—Sughrue, Mion, Zinn, Macpeak & Seas

[57] ABSTRACT

A reagent for measuring a lipase activity comprised of a higher fatty acid ester having the general formula

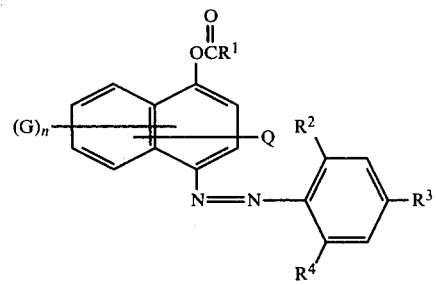

wherein $R^1$ is a straight chain alkyl group; $R^2$ is hydrogen or a halogen atom; $R^3$ and $R^4$ are independently a nitro group, an alkylsulfonyl group, a substituted alkylsulfonyl group or a trifluoromethyl group; G is an —SO$_3$M group or a group having at least one —SO$_3$M where M represents sodium or potassium, or, when $R^4$ has a sulfonic acid group, may be a hydrogen atom; and Q is hydrogen, a halogen atom, an alkyl group, an alkoxy-substituted alkyl group, an alkoxy group, an alkoxy-substituted alkoxy group, a sulfonamido group, a sulfamoyl group, a carbonamido group, a carbamoyl group, or an alkylsulfonyl group. The reagent is capable of releasing a dye on enzymatic hydrolysis by the action of lipase. Because of the released dye has a light absorption zone within the longer wavelength region, it is not substantially disturbed by colored matter contained within blood making it possible to obtain excellent operability and reproducibility in the measurement of lipase activity within blood.

15 Claims, 1 Drawing Figure

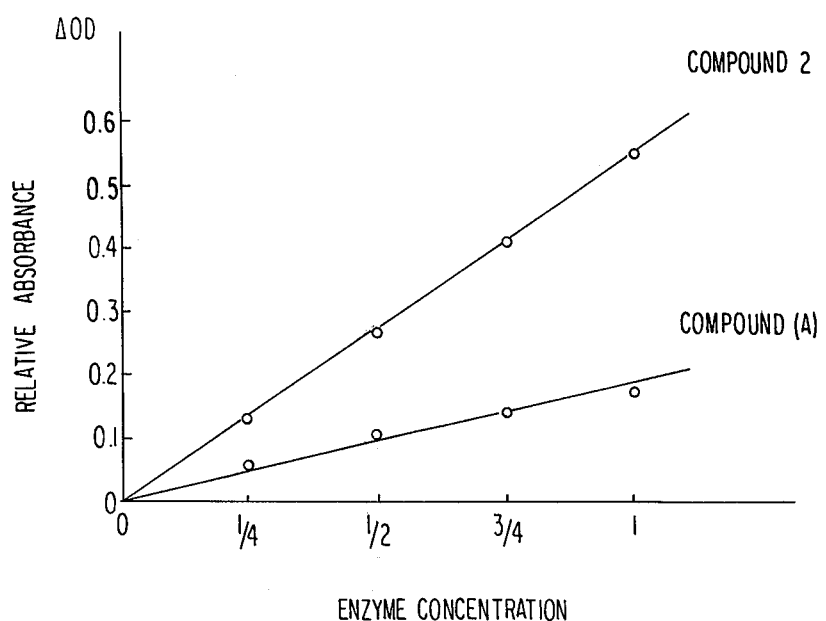
RELATION BETWEEN ENZYME CONCENTRATION AND EXTINCTION COEFFICIENT

REAGENTS FOR MEASURING LIPASE ACTIVITY

FIELD OF THE INVENTION

This invention relates to a reagent for measuring lipase. More particularly, the invention relates to a reagent for measuring lipase comprising a higher fatty acid ester having a function capable of releasing a dye on enzymatic hydrolysis by the action of lipase.

BACKGROUND OF THE INVENTION

Known methods for measuring the activity of lipase include olive oil method (1) and colorimetric methods (2) to (4) as explained below.

(1) The first method involves reacting lipase with emulsified olive oil or synthetic triglyceride as a substrate and neutralizing and titrating the fatty acid formed by hydrolysis, or extracting the fatty acid, coloring sodium diethylthiocarbamate, and then colorimetrically measuring the color. Alternatively, this method may involve reacting lipase with an emulsified substrate and measuring the reduction of turbidity by the hydrolysis. Typical examples are described in J. H. Roe, *Analytical Biochemistry*, 6, 451 (1963).

(2) The second method is a colorimetric method of reacting lipase with an ester of a phenol such as α-naphthol, phenol, p-nitrophenol, etc., and a long chain fatty acid as a substrate, coloring a phenol formed by hydrolysis, and measuring the extent of the hydrolysis. Typical examples are described in F. Whitaker, *Clinica Chimica Acta* 44, 133 (1973).

(3) The third method involves reacting an S-acyl compound such as 3-mercapto-1,2-propanediol tricarboxylic acid ester, etc. with lipase to hydrolyze the S-acyl compound, reacting the thiol formed with 5,5'-dithiobis(2-nitrobenzoic acid) to form a yellow dye, 3-carboxy-4-nitrobenzenethiolate, and measuring the color by colorimetry. These methods are described in, for example, Japanese Patent Application (OPI) Nos. 33694/76, 5309/75, 151594/75 and 159793/75 (the term "OPI" as used herein refers to a "published unexamined Japanese patent applicaton").

(4) The fourth method involves hydrolyzing a higher fatty acid ester of naphtholic orange azo dye by the action of lipase and measuring the orange dye formed by colimetry. Such methods are described in Japanese Patent Application (OPI) No. 46758/79 corresponding to U.S. Pat. No. 4,188,320.

In method (1), it is difficult to prepare a stable and uniform substrate emulsion and there are problems in operability and reproducibility. In methods (2) and (3), since the substrate is insoluble in water, the enzymatic reaction must be performed in the form of emulsion or must be performed in the presence of an organic solvent such as an alcohol. Furthermore, deproteinization must be performed after the reaction, which makes the operation complicated. These difficulties may be overcome in method (4) but since the dye measured by colorimetry in method (4) is orange, the colorimetric method is distributed by colored matters such as dyes in blood. Therefore, it would be more desirable to develop a method which would release a dye having a light absorption zone at a longer wavelength region. Also, further improvement has been desired regarding the spectral extinction coefficient of the released dye having an influence on the measurement sensitivity.

SUMMARY OF THE INVENTION

An object of this invention is to provide a reagent for measuring lipase activity which is excellent in operability and reproducibility of measurement, is not disturbed by colored matters such as dyes in blood, and is excellent with respect to detection sensitivity.

It has been discovered that the foregoing objects of this invention can be effectively attained by a reagent for measuring lipase activity comprising a higher fatty acid ester shown by the following general formula (I)

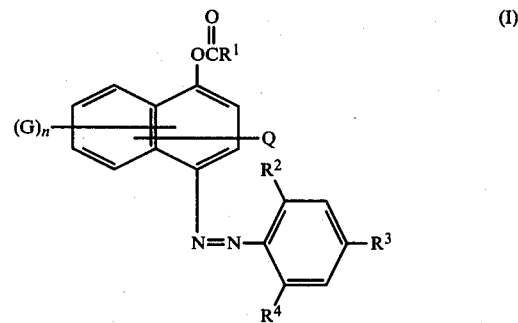

wherein $R^1$ represents a straight chain alkyl group having 9 to 17 carbon atoms; $R^2$ represents a hydrogen atom or a halogen atom; and $R^3$ and $R^4$, may be the same or different, each represents a nitro group, an alkylsulfonyl group having 8 or less carbon atoms, a substituted alkylsulfonyl group having 8 or less carbon atoms, or a trifluoromethyl group; G is $-SO_3M$, or an atomic group having at least one $-SO_3M$, where M represents sodium or potassium, or, when $R^4$ has a sulfonic acid group, may be a hydrogen atom; Q represents a hydrogen atom, a halogen atom, an alkyl group, an alkoxy-substituted alkyl group, an alkoxy group, an alkoxy-substituted alkoxy group, a sulfonamido group, a sulfamoyl group, a carbonamido group, a carbamoyl group, or an alkylsulfonyl group; the carbon atom number of the foregoing substituents is 8 or less; and n is an integer of 1 to 3.

BRIEF DESCRIPTION OF THE DRAWING

The FIGURE is a graph showing the relation between an enzyme concentration and an extinction coefficient, wherein the axis of the ordinate indicates the extinction coefficient O.D. with a blank being a contrast and the axis of abscissa is the concentration of an enzyme solution.

DETAILED DESCRIPTION OF THE INVENTION

Higher fatty acid esters encompassed by general formula (I) above are explained below in detail.

Examples of the alkyl group represented by $R^1$ include an n-nonyl group, an u-undecyl group, an n-tridecyl group, an n-pentadecyl group, an n-heptadecyl group, etc.

Practical examples of the halogen atom represented by $R^2$ in general formula (I) are chlorine, bromine, fluorine, etc.

Examples of the alkylsulfonyl group represented by $R^3$ and $R^4$ include a methylsulfonyl group, an ethylsulfonyl group, a butylsulfonyl group, a heptylsulfonyl group, etc.

Examples of the substituted alkylsulfonyl groups shown by $R^3$ and $R^4$ in general formula (I) are an alkylsulfonyl group substituted by a sulfonic acid group (e.g., a sulfomethylsulfonyl group, a sulfoethylsulfonyl group, a sulfopropylsulfonyl group, etc.), an alkoxy group (e.g., a methoxymethylsulfonyl group, an ethoxymethylsulfonyl group, a methoxyhepthylsulfonyl group, etc.). etc.

The atomic group having —SO$_3$M represented by G in general formula (I) is practically shown by the following formula

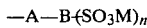

wherein A represents —NHSO$_2$—, —SO$_2$NH—, etc., and B represents a phenyl group, a naphthyl group, etc., and n is an integer of 1 to 3.

More practical examples of G are as follows:

 (G-1)

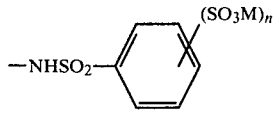 (G-2)

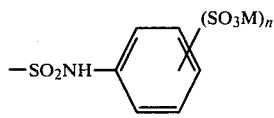 (G-3)

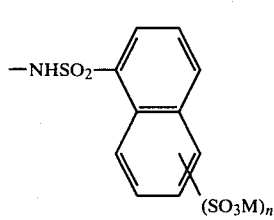 (G-4)

wherein M represents sodium or potassium and n is an integer of 1 to 3.

In foregoing group (G-2) or (G-3), —SO$_3$M is disposed at the ortho-position, meta-position or para-position to —NHSO$_2$— or —SO$_2$NH—. Also, the benzene ring of (G-2) or (G-3) may have a substituent such as an alkyl group having 1 to 4 carbon atoms, a substituted alkyl group having 1 to 4 carbon atoms, an alkoxy group having 1 to 4 carbon atoms, a sulfonamido group, a sulfamoyl group, a carbonamido group, a carbamoyl group, a sulfonic acid group, etc., and in group (G-4), the group —SO$_3$M is disposed at the 3-, 4-, 5-, 6-, 7-, or 8-position of said naphthalene ring. Also, said naphthalene ring may have a substituent such as an alkyl group having 1 to 4 carbon atoms, a substituted alkyl group having 1 to 4 carbon atoms, an alkoxy group having 1 to 4 carbon atoms, a sulfonamido group, a sulfamoyl group, a carbonamido group, a carbamoyl group, a sulfone group, etc.

Practical examples of the halogen atom represented by Q are chlorine, bromine, fluorine, etc.

Examples of the alkyl group represented by Q include a methyl group, an ethyl group, a propyl group, a hexyl group, an octyl group, etc.

Examples of the alkoxy-substituted alkyl group represented by Q include a methoxymethyl group, a methoxypropyl group, an ethoxymethyl group, a butoxypropyl group, etc.

Examples of the alkoxy group represented by Q include a methoxy group, an ethoxy group, a butoxy group, etc.

Examples of the alkoxy-subtituted alkoxy group represented by Q include a methoxymethyl group, a methoxymethyl group, a methoxybutoxy group, etc.

Also, the sulfonamido group is shown by —NH—SO$_2$R$^5$ wherein $R^5$ is an alkyl group having 1 to 8 carbon atoms such as a methyl group, an ethyl group, a propyl group, an isopropyl group, a butyl group, an isobutyl group, a sec-butyl group, a t-butyl group, a hexyl group or an octyl group, a phenyl group, a p-methylphenyl group, etc. The carbonamido group is shown by —NH—COR$^6$ wherein $R^6$ has the same significance as $R^5$. The sulfamoyl group is shown by

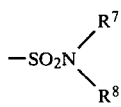

wherein $R^7$ and $R^8$, which may be the same or different, each represents a hydrogen atom or an alkyl group having 1 to 8 carbon atoms. Examples of the alkyl groups include a methyl group, an ethyl group, a propyl group, an isopropyl group, a butyl group, an isobutyl group, a sec-butyl group, a t-butyl group, a hexyl group or octyl group, a phenyl group, a p-methylphenyl group, etc. Furthermore, $R^7$ and $R^8$ may form a ring together with the N atom, such as, for example,

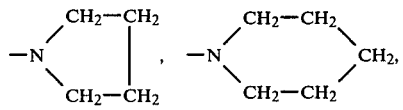

etc. The carbamoyl group as shown by

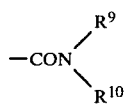

wherein $R^9$ and $R^{10}$ have the same significance as $R^7$ and $R^8$.

Preferred examples of $R^3$ and $R^4$ in general formula (I) are a nitro group, an alkylsulfonyl group having 1 to 8, preferably 1 to 4 carbon atoms, and a substituted alkylsulfonyl group having 1 to 8 carbon atoms.

Preferred examples of G in general formula (I) are (G-1) and (G-2) among the groups illustrated above.

Preferred examples of Q in general formula (I) are a hydrogen atom, a halogen atom, an alkoxy group having 1 to 8 carbon atoms, a sulfonamido grop having 1 to 8 carbon atoms, and a carbonamido group having 1 to 8 carbon atoms.

Furthermore, among the groups shown by $R^3$ and $R^4$ in general formula (I), a nitro group or a methylsulfonyl group is particularly preferred. Also, among the groups shown by $R^2$, the particularly preferred group is a hydrogen atom. In the combinations of $R^3$, $R^4$ and $R^2$, the combinations wherein $R^4$ is a methylsulfonyl group, $R^3$ is a nitro group, and $R^2$ is a hydrogen atom is most preferred since in this case the molecular extinction coefficient of the dye released by the hydrolysis is large, the maximum visible absorption wavelength is long, and such a raw material is easily available. Among the groups shown by G, the particularly preferred group is the group foregoing (G-2) wherein —SO$_3$M is at the metaposition of the benzene ring to —NHSO$_2$—. Moreover, it is preferred that the group shown by (G-2) be at the peri-position of the naphthalene ring of the compound shown by general formula (I) to the azo group since in this case, the group contributes to sharpening the visible absorption band of the dye released by hydrolysis and increases the molecular extinction coefficient. Among the groups shown by Q, the particularly preferred group is a hydrogen atom or a methanesulfonamido group and it is preferred that the methanesulfonamido group be at the peri-position of the naphthalene ring of the compound shown by general formula (I) to the azo group since in this case, the group contributes to sharpening the visible absorption band of the dye released by hydrolysis and increases the molecular extinction coefficient.

Then, typical examples of the high fatty acid esters of this invention encompassed by general formula (I) are shown below:

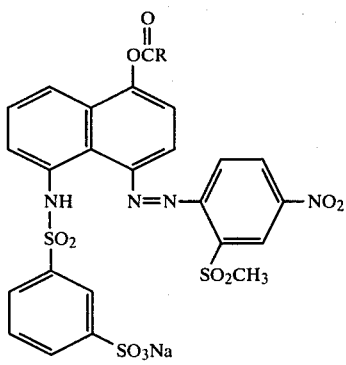

The compound shown by the above formula wherein R is n—C$_9$H$_{19}$.

COMPOUND 2

The compound of the foregoing formula of Compound 1 wherein R is n—C$_{11}$H$_{23}$.

COMPOUND 3

The compound of the foregoing formula of Compound 1 wherein R is n—C$_{13}$H$_{27}$.

COMPOUND 4

The compound of the foregoing formula of Compound I wherein R is n—C$_{15}$H$_{31}$.

COMPOUND 5

The compound of the foregoing formula of Compound I wherein R is n—C$_{17}$H$_{35}$.

COMPOUND 6

The compound of the foregoing formula of Compound 1 wherein R is n—C$_9$H$_{19}$ and K is substituted for Na.

COMPOUND 7

The compound of the foregoing formula of Compound 1 wherein R is n—C$_{11}$H$_{23}$ and K is substituted for Na.

COMPOUND 8

The compound of the foregoing formula of Compound 1 wherein R is n—C$_{13}$H$_{27}$ and K is substituted for Na.

COMPOUND 9

The compound of the foregoing formula of Compound 1 wherein R is n—C$_{15}$H$_{31}$ and K is substituted for Na.

COMPOUND 10

The compound of the foregoing formula of Compound 1 wherein R is n—C$_{17}$H$_{35}$ and K is substituted for Na.

COMPOUND 11

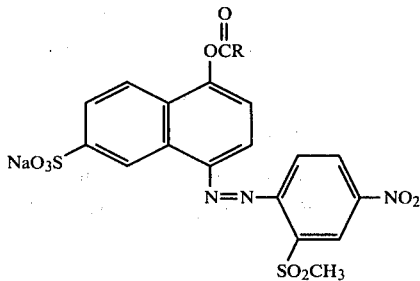

The compound shown by the above formula wherein R is n—C$_9$H$_{19}$.

COMPOUND 12

The compound of the foregoing formula of Compound 11 wherein R is n—C$_{11}$H$_{23}$.

COMPOUND 13

The compound of the foregoing formula of Compound 11 wherein R is n—C$_{13}$H$_{27}$.

COMPOUND 14

The compound of the foregoing formula of Compound 11 wherein R is n—C$_{15}$H$_{31}$.

COMPOUND 15

The compound of the foregoing formula of Compound 11 wherein R is n—C$_{17}$H$_{35}$.

COMPOUND 16

The compound of the foregoing formula of Compound 11 wherein R is n—C$_{11}$H$_{23}$ and K is substituted for Na.

COMPOUND 17

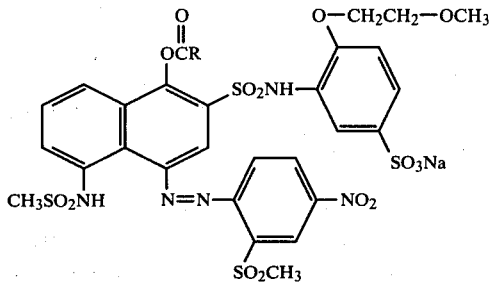

The compound of the above formula wherein R is n—$C_9H_{19}$.

COMPOUND 18

The compound of the foregoing formula of Compound 17 wherein R is n—$C_{11}H_{23}$.

COMPOUND 19

The compound of the foregoing formula of Compound 17 wherein R is n—$C_{13}H_{27}$.

COMPOUND 20

The compound of the foregoing formula of Compound 17 wherein R is n—$C_{15}H_{31}$.

COMPOUND 21

The compound of the foregoing formula of Compound 17 wherein R is n—$C_{17}H_{35}$.

COMPOUND 22

The compound of the foregoing formula of Compound 17 wherein R is n—$C_{11}H_{23}$ and K is substituted for Na.

COMPOUND 23

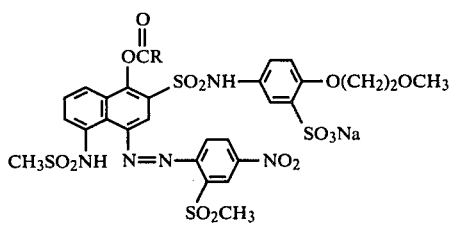

The compound of the above formula wherein R is n—$C_9H_{19}$.

COMPOUND 24

The compound of the foregoing formula of Compound 23 wherein R is n—$C_{11}H_{23}$.

COMPOUND 25

The compound of the foregoing formula of Compound 23 wherein R is n—$C_{13}H_{27}$.

COMPOUND 26

The compound of the foregoing formula of Compound 23 wherein R is n—$C_{15}H_{31}$.

COMPOUND 27

The compound of the foregoing formula of Compound 23 wherein R is n—$C_{17}H_{35}$.

COMPOUND 28

The compound of the foregoing formula of Compound 23 wherein R is n—$C_{11}H_{23}$ and K is substituted for Na.

COMPOUND 29

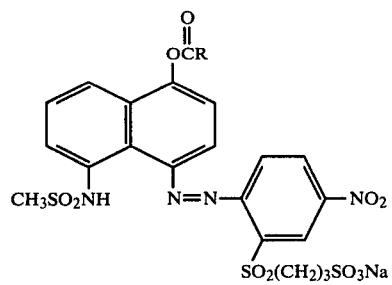

The compound of the above formula wherein R is n—$C_9H_{19}$.

COMPOUND 30

The compound of the foregoing formula of Compound 29 wherein R is n—$C_{11}H_{23}$.

COMPOUND 31

The compound of the foregoing formula of Compound 29 wherein R is n—$C_{13}H_{27}$.

COMPOUND 32

The compound of the foregoing formula of Compound 29 wherein R is n—$C_{15}H_{31}$.

COMPOUND 33

The compound of the foregoing formula of Compound 29 wherein R is n—$C_{17}H_{35}$.

COMPOUND 34

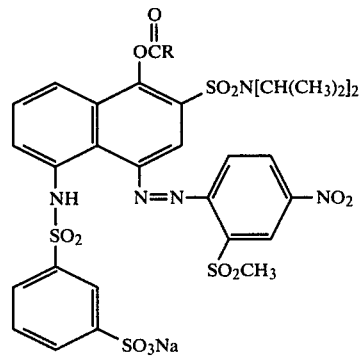

The compound of the above formula wherein R is n—$C_9H_{19}$.

COMPOUND 35

The compound of the foregoing formula of Compound 34 wherein R is n—$C_{11}H_{23}$.

COMPOUND 36

The compound of the foregoing formula of Compound 34 wherein R is n—$C_{13}H_{27}$.

COMPOUND 37

The compound of the foregoing formula of Compound 34 wherein R is n—$C_{15}H_{31}$.

COMPOUND 38

The compound of the foregoing formula of Compound 34 wherein R is n—$C_{17}H_{35}$.

COMPOUND 39

The compound of the foregoing formula of Compound 34 wherein R is n—$C_{11}H_{23}$ and K is substituted for Na.

COMPOUND 40

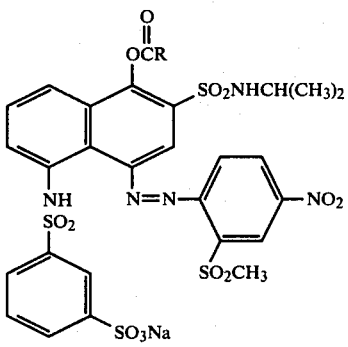

The compound of the above formula wherein R is n—$C_9H_{19}$.

COMPOUND 41

The compound of the foregoing formula of Compound 40 wherein R is n—$C_{11}H_{23}$.

COMPOUND 42

The compound of the foregoing formula of Compound 40 wherein R is n—$C_{13}H_{27}$.

COMPOUND 43

The compound of the foregoing formula of Compound 40 wherein R is n—$C_{15}H_{31}$.

COMPOUND 44

The compound of the foregoing formula of Compound 40 wherein R is n—$C_{17}H_{35}$.

COMPOUND 45

The compound of the foregoing formula of Compound 40 where R is n—$C_{11}H_{23}$ and K is substituted for Na.

COMPOUND 46

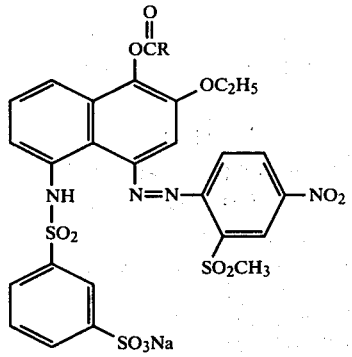

The compound of the above formula wherein R is n—$C_9H_{19}$.

COMPOUND 47

The compound of the foregoing formula of Compound 46 wherein R is n—$C_{11}H_{23}$.

COMPOUND 48

The compound of the foregoing formula of Compound 46 wherein R is n—$C_{13}H_{27}$.

COMPOUND 49

The compound of the foregoing formula of Compound 46 wherein R is n—$C_{15}H_{31}$.

COMPOUND 50

The compound of the foregoing formula of Compound 46 wherein R is n—$C_{17}H_{35}$.

COMPOUND 51

The compound of the foregoing formula of Compound 46 wherein R is n—$C_{11}H_{23}$ and K is substituted for Na.

COMPOUND 52

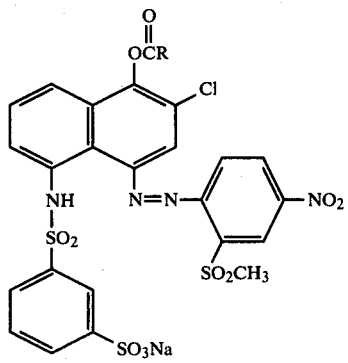

The compound of the above formula wherein R is n—$C_9H_{19}$.

COMPOUND 53

The compound of the foregoing formula of Compound 52 wherein R is n—$C_{11}H_{23}$.

COMPOUND 54

The compound of the foregoing formula of Compound 52 wherein R is n—$C_{13}H_{27}$.

COMPOUND 55

The compound of the foregoing formula of Compound 52 wherein R is n—$C_{15}H_{31}$.

COMPOUND 56

The compound of the foregoing formula of Compound 52 wherein R is n—$C_{17}H_{35}$.

COMPOUND 57

The compound of the foregoing formula of Compound 52 wherein R is n—$C_{11}H_{23}$.

COMPOUND 58

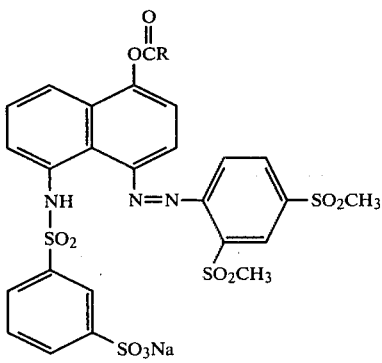

The compound of the above formula wherein R is n—$C_9H_{19}$.

COMPOUND 59

The compound of the foregoing formula of Compound 58 wherein R is n—$C_{11}H_{23}$.

COMPOUND 60

The compound of the foregoing formula of Compoung 58 wherein R is n—$C_{15}H_{31}$.

COMPOUND 61

The compound of the foregoing formula of Compound 58 wherein R is n—$C_9H_{19}$ and K is substituted for Na.

COMPOUND 62

The compound of the foregoing formula of Compound 58 wherein R is n—$C_{13}H_{29}$ and K is substituted for Na.

COMPOUND 63

The compound of the foregoing formula of Compound 58 wherein R is n—$C_{17}H_{35}$ and K is substituted for Na.

COMPOUND 64

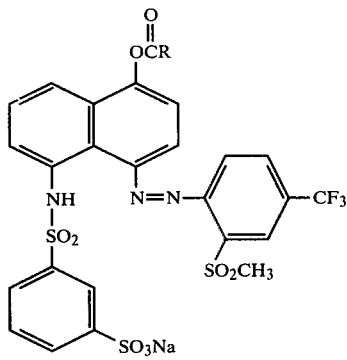

The compound of the above formula wherein R is n—$C_9H_{19}$.

COMPOUND 65

The compound of the foregoing formula of Compound 64 wherein R is n—$C_{13}H_{27}$.

COMPOUND 66

The compound of the foregoing formula of Compound 64 wherein R is n—$C_{17}H_{35}$.

COMPOUND 67

The compound of the foregoing formula of Compound 64 wherein R is n—$C_{11}H_{23}$ and K is substituted for Na.

COMPOUND 68

The compound of the foregoing formula of Compound 64 wherein R is n—$C_{15}H_{31}$ and K is substituted for Na.

COMPOUND 69

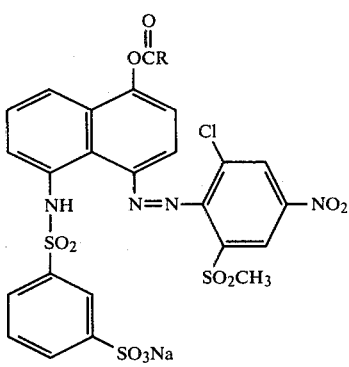

The compound of the above formula wherein R is n—$C_9H_{19}$.

COMPOUND 70

The compound of the foregoing formula of Compound 69 wherein R is n—$C_{11}H_{23}$.

COMPOUND 71

The compound of the foregoing formula of Compound 69 wherein R is n—$C_{13}H_{27}$.

COMPOUND 72

The compound of the foregoing formula of Compound 69 wherein R is n—$C_{15}H_{31}$.

Compound 73

The compound of the foregoing formula of Compound 69 wherein R is n—$C_{17}H_{35}$.

COMPOUND 74

The compound of the foregoing formula of Compound 69 wherein R is n—$C_9H_{19}$ and K is substituted for Na.

Compound 75

The compound of the foregoing formula of Compound 69 wherein R is n—$C_{11}H_{23}$ and K is substituted for Na.

COMPOUND 76

The compound of the foregoing formula of Compound 69 wherein R is n—$C_{13}H_{27}$ and K is substituted for Na.

COMPOUND 77

The compound of the foregoing formula of Compound 69 wherein R is n—$C_{15}H_{31}$ and K is substituted for Na.

Of the above compounds, Compounds 1 to 10 are particularly preferred since they release dyes showing a sharp absorption and large $\epsilon$ and having high solubility.

These compounds can be easily prepared by ordinary methods for preparing carboxylic acid aryl esters. That is, the compound can be prepared by reacting a corresponding azo dye with an anhydride or halide of a higher fatty acid in a solvent such as an amide, e.g., N,N-dimethylformamide, N,N-dimethylacetamide, N-methylpyrrolidone, etc.; a nitrile such as acetonitrile, etc.; or an aromatic cyclic amine such as pyridine, etc., in the presence of an acid catching agent such as pyridine, etc. The purification of the objective material is performed by an ordinary manner. Also, each azo dye can be prepared by a coupling reaction of a corresponding naphthol derivative and a corresponding diazonium salt according to an ordinary manner. However, when the substituents $R^3$ and $R^4$ of the portions originated in the diazonium salt in the compound of this invention are strong electron attractive groups, it is preferable to use a so-called nitrosylsulfuric acid method (e.g., Yutaka Hosoda, *Sin Senryo Kagaku* (*New Dye Chemistry*), 4th Edition, page 115, Gihodo (Tokyo, 1965), Mary Fiesier and Levis Fiesier, *Reagents for Organic Synthesis*, Vol. 1, page 755 and Vol. 2, pages 299–300, Weiley Interscience (New York, 1969) and Stanley R. Sandler and Wols Karo, *Organic Functional Group Preparation*, Vol. 2, pages 295–296, Academic Press (New York, 1971)), for the preparation of the diazonium salt. These reactions proceed at room temperature under normal pressure for 1 to 4 hours but, if necessary, the reaction system may be heated.

For example, each of Compounds 1 to 10, 29 to 33 and 46 to 77 can be easily prepared by dissolving each corresponding naphtholazo dye in N,N-dimethylacetamide, adding a halide of a corresponding higher fatty acid and pyridine to the solution, and performing the reaction (for 1 to 2 hours at room temperature). Also, each of Compounds 11 to 16 can be easily prepared by dissolving a corresponding naphtholazo dye in pyridine, adding a halide of a corresponding higher fatty acid to the solution, and performing the reaction (for 1 to 2 hours at room temperature). Furthermore, each of Compounds 17 to 28, 34 to 45 can be easily prepared by suspending a corresponding naphtholazo dye in acetonitrile, adding a halide of a corresponding higher fatty acid to the suspension, and performing the reaction (for 1 to 3 hours at room temperature).

The compounds of this invention thus obtained are excellent as a reagent for measuring lipase activity.

That is, when the compounds of this invention are used as a reagent for measuring lipase activity, the compounds of this invention have the following merits (a), (b) and (c) as compared to conventional compounds.

(a) Since the compound is colored in green or blue, the activity of lipase, etc., can be measured without being disturbed by the visible absorption of dyes in blood.

(b) Since the molecular absorption coefficient of the dye released by the hydrolysis of the compound is large (e.g., about 3 times the molecular absorption coefficient of the dye released from the compound described in Japanese Patent Application (OPI) No. 46758/79, corresponding to U.S. Pat. No. 4,188,320, the measurement can be performed at a high qualitative sensitivity.

(c) Since the compound is soluble in water, the measurement can be performed in an aqueous solution without need of an organic solvent or sodium cholate and hence a wide measurement condition can be selected.

Synthesis examples of the compounds used in this invention are illustrated below.

SYNTHESIS EXAMPLE 1

Synthesis of Compound 2

In 100 ml of N,N-dimethylacetamide was dissolved 6.3 g of sodium 3-{N-[5-hydroxy-8-(2-methylsulfonyl-4-nitrophenylazo)naphthyl]sulfamoyl}benzenesulfonate and after adding 14 ml of lauroyl chloride and 4 ml of pyridine to the solution, the mixture was stirred for 1.5 hours at room temperature. Then, the reaction mixture was poured in 300 ml of a saturated aqueous sodium chloride solution and solids thus formed were collected by filtration. To the solids was added 200 ml of methanol and after filtering off insoluble matters, the filtrate was purified by a Cephadex column chromatography (LH-20, solvent: methanol).

The amount of the product was 160 mg.

$\lambda_{max} = 550$ nm, $\epsilon = 8.25 \times 10^3$ (in 1/15 M phosphoric acid buffer of pH 8).

TABLE 1

|  | Result of Elemental Analysis | | |
|---|---|---|---|
|  | C | H | N |
| Calculated (%) | 51.79 | 4.90 | 6.88 |
| Found (%) | 51.84 | 4.85 | 6.91 |

SYNTHESIS EXAMPLE 2

Synthesis of Compound 24

In 100 ml of acetonitrile was dispersed 2 g of sodium 2-(2-methoxyethoxy)-5-[1-hydroxy-5-methanesulfonamido-4-(2-methylsulfonyl-4-nitrophenylazo)-2-naphthylsulfonamido]benzenesulfonate and after adding thereto 7 ml of lauroyl chloride, the mixture was stirred for 2 hours at room temperature. The red precipitates formed were collected by filtration, washed with acetonitrile, and dried.

The amount of the product was 1.54 g.

$\lambda_{max} = 480$ nm, $\epsilon = 1.22 \times 10^4$ (measured in methanol).

TABLE 2

|  | Result of Elemental Analysis | | |
|---|---|---|---|
|  | C | H | N |
| Calculated (%) | 49.70 | 5.21 | 7.47 |
| Found (%) | 49.51 | 5.11 | 7.40 |

SYNTHESIS EXAMPLE 3

Synthesis of Compound 18

In 20 ml of acetonitrile was dispersed 0.5 g of sodium 2-(4-methoxyethoxy)-5-[1-hydroxy-5-methanesulfonamido-4-(2-methylsulfonyl-4-nitrophenylazo)-2-naphthylsulfonamido]benzenesulfonate and after adding thereto 1 ml of lauroyl chloride, the mixture was stirred for 2 hours at room temperature. The red precipitates formed were collected by filtration, washed with acetone, and dried.

The amount of the product was 0.52 g.

$\lambda_{max}$=481 nm, $\epsilon$=1.80×10⁴ (measured in methanol).

TABLE 3

| | Result of Elemental Analysis | | |
|---|---|---|---|
| | C | H | N |
| Calculated (%) | 49.29 | 5.02 | 7.31 |
| Found (%) | 49.51 | 5.11 | 7.40 |

SYNTHESIS EXAMPLE 4

Synthesis of Compounds 7, 30, 47, and 53

By following the same reaction, separation, and purification procedures as in Synthesis Example 1 using the naphtholazo dyes corresponding to the abovedescribed objective compounds and the halides of the higher fatty acids corresponding to the aforesaid compounds in place of sodium 3-{N-[5-hydroxynaphthyl-8-(2-methylsulfonyl-4-nitrophenylazo)]sulfonyl}benzenesulfonate and lauroyl chloride, Compounds 7, 30, 47 and 53 were obtained.

In this case, potassium 3-{N-[5-hydroxy-8-(2-methylsulfonyl-4-nitrophenylazo)naphthyl]sulfamoyl}benzenesulfonate and lauroyl chloride were used as the raw materials for producing Compound 7; sodium 3-[2-(4-hydroxy-8-methanesulfonamidoazonaphthyl)-5-nitrophenylsulfonyl]propanesulfonate and lauroyl chloride were used for Compound 30; sodium 3-{N-[6-ethoxy-5-hydroxy-8-(2-methylsulfonyl-4-nitrophenylazo)naphthyl]sulfamoyl}benzenesulfonate and lauroyl chloride were used for Compound 47; and sodium 3-{N-[6-chloro-5-hydroxy-8-(2-methylsulfonyl-4-nitrophenylazo)naphthyl]sulfamoyl}benzenesulfonate and lauroyl chloride were used for Compound 53.

The results of the elemental analysis of the products thus obtained are shown in Table 4.

TABLE 4

| Compound | Results of Elemental Analysis | | | |
|---|---|---|---|---|
| | | C | H | N |
| 7 | Calculated (%) | 50.68 | 4.81 | 6.72 |
| | Found (%) | 50.83 | 4.75 | 6.77 |
| 30 | Calculated (%) | 49.58 | 5.34 | 7.12 |
| | Found (%) | 49.47 | 5.32 | 7.21 |
| 47 | Calculated (%) | 51.72 | 5.01 | 6.42 |
| | Found (%) | 51.98 | 5.07 | 6.55 |
| 53 | Calculated (%) | 49.61 | 4.50 | 6.47 |
| | Found (%) | 49.73 | 4.53 | 6.63 |

SYNTHESIS EXAMPLE 5

Synthesis of Compounds 35, 36 and 41

By following the same reaction, separation, and purification procedures as in Synthesis Example 2 using the naphtholazo dyes corresponding to the aforesaid objective compounds and the halides of the higher fatty acids corresponding to the aforesaid objective compounds in place of sodium 2-(2-methoxyethoxy)-5-[1-hydroxy-5-methanesulfonamido-4-(2-methylsulfonyl-4-nitrophenylazo)-2-naphthylsulfonamido]benzenesulfonate and lauroyl chloride, Compounds 35, 36 and 41 were obtained.

In this case, sodium 3-{N-[5-hydroxy-8-(2-methylsulfonyl-4-nitrophenylazo)-6-(N,N-diisopropylsulfamoyl)-naphthyl]sulfamoyl}benzenesulfonate and lauroyl chloride or myristoyl chloride were used as the raw materials for producing Compound 35 or 36, and sodium 3-{N-[5-hydroxy-8-(2-methylsulfonyl-4-nitrophenylazo)-6-(N-isopropylsulfamoyl)naphthyl]sulfamoyl}benzenesulfonate and lauroyl chloride were used for producing Compound 41.

The results of the elemental analysis of the products obtained are shown in Table 5.

TABLE 5

| Compound | Results of Elemental Analysis | | | |
|---|---|---|---|---|
| | | C | H | N |
| 35 | Calculated (%) | 52.09 | 5.47 | 7.30 |
| | Found (%) | 52.27 | 5.56 | 7.43 |
| 36 | Calculated (%) | 53.41 | 5.89 | 7.13 |
| | Found (%) | 53.24 | 5.82 | 7.22 |
| 41 | Calculated (%) | 50.52 | 5.20 | 7.71 |
| | Found (%) | 50.71 | 5.15 | 7.78 |

SYNTHESIS EXAMPLE 6

Synthesis of Compounds 12, 13 and 14

By following the same reaction, separation, and purification procedures as in Synthesis Example 1 using corresponding naphtholazo dyes in place of sodium 3-{N-[5-hydroxynaphthyl-8-(2-methylsulfonyl-4-nitrophenylazo)]sulfamoyl}benzenesulfonate and N,N-dimethylacetamide, Compounds 12, 13 and 14 were obtained.

In this case, sodium 1-hydroxy-4-(2-methylsulfonyl-4-nitrophenylazo)naphthalene-6-sulfonate and lauroyl chloride, myristoyl chloride, or palmitoyl chloride were used as the raw materials for Compound 12, 13 or 14, respectively.

The results of the elemental analysis of the compounds obtained are shown in Table 6.

TABLE 6

| Compound | Results of Elemental Analysis | | | |
|---|---|---|---|---|
| | | C | H | N |
| 12 | Calculated (%) | 52.91 | 5.30 | 6.37 |
| | Found (%) | 53.12 | 5.23 | 6.41 |
| 13 | Calculated (%) | 54.59 | 5.74 | 6.01 |
| | Found (%) | 54.45 | 5.60 | 6.15 |
| 14 | Calculated (%) | 55.59 | 6.02 | 5.87 |
| | Found (%) | 55.68 | 5.95 | 5.90 |

Then, the invention will be explained in detail based on the following examples but the invention is not limited to them.

EXAMPLE 1

Preparation of Substrate Solution

To Compound 2 (6.48 mg) was added sodium laurylsulfate phosphoric acid buffer solution (to 288 mg of sodium laurylsulfate was added 1/15 M phosphoric acid buffer solution of pH 8 to form 100 ml of a solution) to form 5 ml of a solution. To 1 ml of the solution was added 1 ml of an aqueous 20% sodium cholate solution and a sodium laurylsulfate phosphoric acid buffer solution to form 10 ml of a solution.

Preparation of Enzyme Solution

To 0.4 g of crude lipase (Sigma Chemical Type II) was added 20 ml of distilled water and insoluble matters were filtered off. The solution was diluted to ¼, ½, and ¾ to provide four kinds of enzyme solutions.

Measurement of Enzyme Activity

To 1 ml of the foregoing substrate solution was added 0.1 ml of the foregoing enzyme solution and after incubating for 30 minutes 37° C., 3 ml of an aqueous 10% sodium cholate solution was added and then the extinction coefficient was measured. In addition, a blank solution was prepared by adding 0.1 ml of distilled water in place of the aforesaid enzyme solution in the above procedure and processing the mixture by the same manner as above and the difference in extinction coefficient between the foregoing sample and the blank sample was determined.

The result of this invention is shown in the FIGURE together with comparison cases of using a conventional reagent (A) shown below, U.S. Pat. No. 4,188,320) and of using the foregoing enzyme solution.

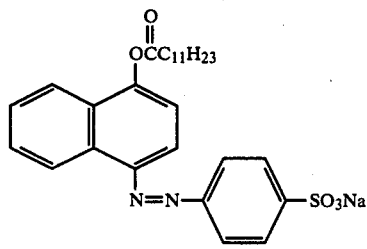

From the FIGURE, it is understood that the measurement sensitivity increases about 3 times as compared with a conventional reagent. Therefore, when the determination of lipase in a serum using the compound of this invention as a reagent for clinical test, the amount of the serum may be less than the case of using the conventional method and the burden of a patient can be lightened.

Visible Absorption Spectrum of Released Dye

The absorption values of Dye (D-3) released from Compound 3 of this invention and Dye (D-A) released from Comparison Sample (A) in a medium under the same condition of the blank test solution in Example 1 are shown in Table 7. From the values in Table 7, it is understood that Dye (D-3) released from the compound of this invention is greatly superior to Dye (D-A) released from the conventional comparison compound in the point that Dye (D-3) has the absorption maximum at a longer wavelength region and the molecular extinction coefficient of the dye is larger.

TABLE 7

| | Visible Absorption Value of Dye | |
| --- | --- | --- |
| Dye | Absorption Maximum Wavelength (nm) | Spectral Extinction Coefficient |
| D-3 | 644 | $6.9 \times 10^4$ |
| D-A | 475 | $2.2 \times 10^4$ |

(The values in a sodium laurylsulfate phosphoric acid buffer solution (pH=8.0) in the presence of sodium cholate.)

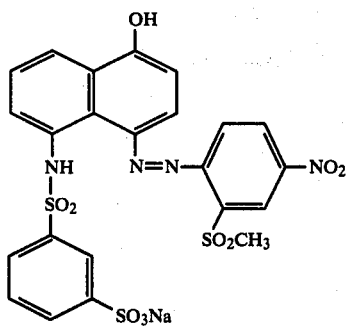

Dye (D-3)

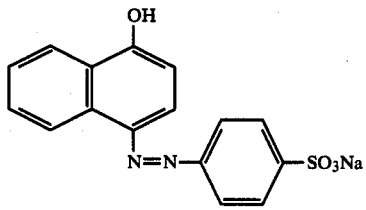

Dye (D-A)

EXAMPLE 2

Preparation of Substrate Solution

To Compound 18 (6.48 mg) was added a sodium laurylsulfate phosphoric acid buffer solution (to 288 mg of sodium laurylsulfate was added 1/15 M phosphoric acid buffer solution of pH 8 to form 100 ml of a solution) to form 5 ml of a solution. To 1 ml of the solution were added 1 ml of an aqueous 20% sodium cholate and a sodium laurylsulfate phosphoric acid buffer solution to form 10 ml of a solution.

Preparation of Enzyme Solution

To 0.4 g of crude lipase (Sigma Chemical Type II) was added 20 ml of distilled water and insoluble matters were filtered off. The solution was diluted to ¼, ½, and ¾ to provide four kinds of enzyme solutions.

Measurement of Enzyme Activity

To 1 ml of the foregoing substrate solution was added 0.1 ml of the foregoing enzyme solution and after incubating for 30 minutes at 37° C., 3 ml of an aqueous 10% sodium cholate solution was added to the mixture and the extinction coefficient was measured. In addition, a blank test solution was prepared by adding 0.1 ml of distilled water in place of the foregoing enzyme solution and processing as in the above manner. The difference in extinction coefficient between the test sample and the blank test sample was determined.

From the results thus obtained, a good relation between the enzyme concentration and extinction coefficient was obtained when using Compound 2 in Example 1.

Visible Absorption Spectrum of Released Dye

The absorption values of Dye (D-18) released from Compound 18 of this invention in a medium under the same condition as the blank test solution in Example 1 are shown in Table 8.

TABLE 8

| | Visible Absorption Value of Dye | |
|---|---|---|
| Dye | Absorption Maximum Wavelength (nm) | Spectral Extinction Coefficient |
| D-18 | 646 | $4.3 \times 10^4$ |

(The value in a sodium laurylsulfate phosphoric acid buffer solution (pH=8.0) in the presence of sodium cholate.)

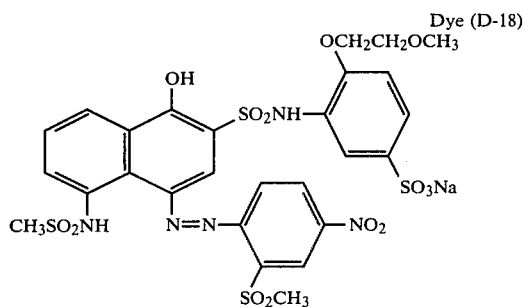

Dye (D-18)

From the values in Table 8, it is understood that Dye (D-18) released from the compound of this invention is greatly superior to Dye (D-A) released from the conventional compound shown in Example 1 in the point that Dye (D-18) has the absorption maximum at a longer wavelength region and the spectral extinction coefficient is larger.

EXAMPLE 3

Preparation of Substrate Solution

To Compound 24 (6.48 mg) was added a sodium laurylsulfate phosphoric acid buffer solution (to 288 mg of sodium laurylsulfate was added a 1/15 M phosphoric acid solution of pH 8 to form 100 ml of a solution) to form 5 ml of a solution. To 1 ml of the solution were added 1 ml of an aqueous 20% sodium cholate solution and a sodium laurylsulfate phosphoric acid buffer solution to form 10 ml of a solution.

Preparation of Enzyme Solution

To 0.4 g of crude lipase (Sigma Chemical Type II) was added 20 ml of distilled water and insoluble material was filtered off. The solution was diluted to $\frac{1}{4}$, $\frac{1}{2}$ and $\frac{3}{4}$ to provide 4 kinds of enzyme solutions.

Measurement of Enzyme Activity

To 1 ml of the foregoing substrate solution was added 0.1 ml of the foregoing enzyme solution and after incubating for 30 minutes at 37° C., 3 ml of an aqueous 10% sodium cholate solution was added and the extinction coefficient was measured. In addition, a blank test sample solution was prepared by adding 0.1 ml of distilled water in place of the aforesaid enzyme solution and processing as above. The difference in extinction coefficient between the test sample and the blank test sample was determined.

From the results thus obtained, a good relation between the enzyme concentration and extinction coefficient, the same as when using Compound 2 in Example 1, was obtained.

Visible Absorption Spectrum of Released Dye

The absorption values of Dye (D-24) released from Compound 24 of this invention in the medium under the same condition as the blank test solution in Example 1 are shown in Table 9.

TABLE 9

| | Visible Absorption Value of Dye | |
|---|---|---|
| Dye | Absorption Maximum Wavelength | Spectral Extinction Coefficient |
| D-24 | 646 nm | $4.2 \times 10^4$ |

(The value in a sodium laurylsulfate phosphoric acid buffer solution (pH=8.0) in the presence of sodium cholate.)

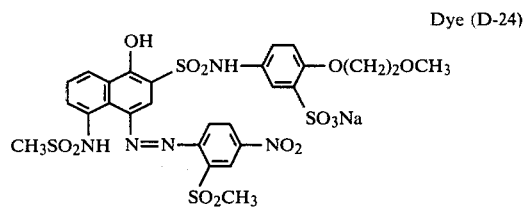

Dye (D-24)

From the values shown in Table 9, it is understood that Dye (D-24) released from the compound of this invention is greatly superior to Dye (D-A) released from the conventional compound shown in Example 1 in the point that Dye (D-24) has the absorption maximum at a longer wavelength region and the spectral extinction coefficient is larger.

While the invention has been described in detail and with reference to specific embodiments thereof, it will be apparent to one skilled in the art that various changes and modifications can be made therein without departing from the spirit and scope thereof.

What is claimed is:

1. A reagent for measuring a lipase activity comprising a higher fatty acid ester represented by the general formula

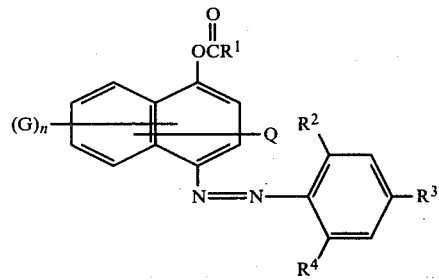

wherein $R^1$ represents an alkyl group having 9 to 17 carbon atoms; $R^2$ represents a hydrogen atom or a halogen atom; $R^3$ and $R^4$, which may be the same or different, each represents a nitro group, an alkylsulfonyl group having 1 to 8 carbon atoms, an alkylsulfonyl group having 1 to 8 carbon atoms substituted by a sulfo group or an alkoxy group, or a trifluoromethyl group; G represents —$SO_3M$ or an atomic group having at least one —$SO_3M$, where M represents sodium or potassium, or, when $R^4$ has a sulfonic acid group, may be a hydrogen atom; Q represents a hydrogen atom, a halogen atom, an alkyl group, an alkoxy-substituted alkyl group, an alkoxy group, an alkoxy-substituted alkoxy group, a sulfonamido group, a sulfamoyl group, a carbonamido group, a carbamoyl group, or an alkylsulfonyl group; the carbon atom number of these substituents being 8 or less than 8; and n is an integer of 1 to 3.

2. A reagent as claimed in claim 1, wherein $R^2$ is selected from the group consisting of hydrogen, chlorine, bromine and fluorine; $R^3$ and $R^4$, which may be the same or different, each is selected from the group consisting of a nitro group, an alkylsulfonyl group having 1 to 8 carbon atoms, and an alkyl-sulfonyl group having 1 to 8 carbon atoms substituted by a sulfo group or an alkoxy group, G is selected from the group consisting of hydrogen, —$SO_3M$,

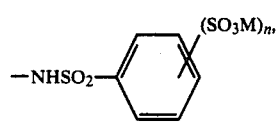

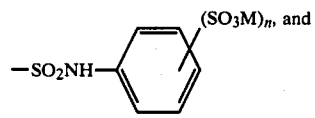

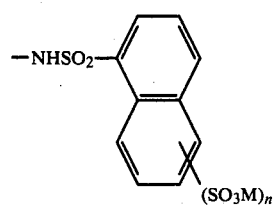

where the benzene ring or the naphthalene ring may have a substituent selected from the group consisting of an alkyl group, an alkoxy group, an alkoxy group substituted by an alkoxy group, a sulfonamido group, a sulfamoyl group, a carbonamido group, a carbamoyl group, and a sulfonic acid group;

M represents sodium or potassium; and n is an integer of 1 to 3;

Q is selected from the group consisting of hydrogen, chlorine, bromine, fluorine, and a sulfonamido group;

and when G is hydrogen, $R^4$ is a sulfonic acid group substituted alkylsulfonyl group.

3. A reagent as claimed in claim 2, wherein $R^3$ and $R^4$ are independently selected from the group consisting of a nitro group, and a methylsulfonyl group.

4. A reagent as claimed in claim 2, wherein $R^4$ is a methylsulfonyl group, $R^3$ is a nitro group and $R^2$ is hydrogen.

5. The reagent as claimed in claim 1 wherein $R^1$ represents a straight chain alkyl group having 9 to 17 carbon atoms.

6. The reagent as claimed in claim 2 wherein $R^1$ represents a straight chain alkyl group having 9 to 17 carbon atoms.

7. A reagent as claimed in claim 1 comprising a higher fatty acid ester represented by the formula

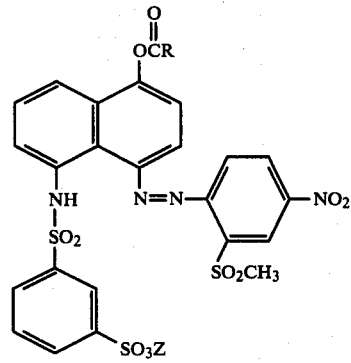

wherein Z is Na or K, and R is n—$C_{11}H_{23}$.

8. A reagent as claimed in claim 1 comprising a higher fatty acid ester represented by the formula

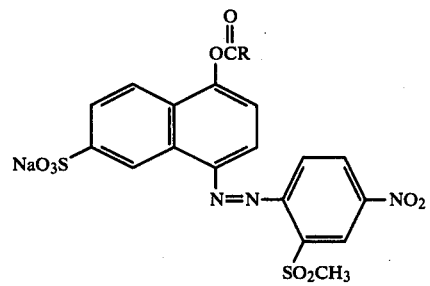

wherein R is n—$C_{11}H_{23}$, n—$C_{13}H_{27}$ or n—$C_{15}H_{31}$.

9. A reagent as claimed in claim 1 comprising a higher fatty acid ester represented by the formula

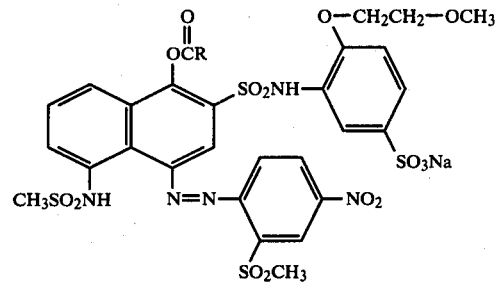

wherein R is n—$C_{11}H_{23}$.

10. A reagent as claimed in claim 1 comprising a higher fatty acid ester represented by the formula

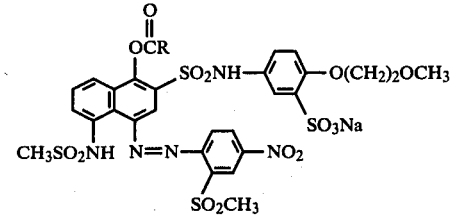

wherein R is n—$C_{11}H_{23}$.

11. A reagent as claimed in claim 1 comprising a higher fatty acid ester represented by the formula

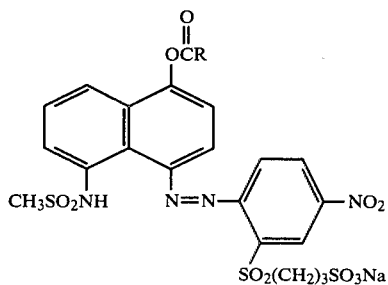

wherein R is n—$C_{11}H_{23}$.

12. A reagent as claimed in claim 1 comprising a higher fatty acid ester represented by the formula

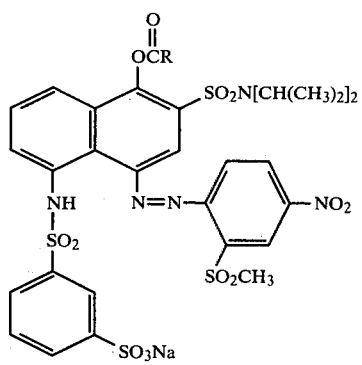

wherein R is n—$C_{11}H_{23}$ or n—$C_{13}H_{27}$.

13. A reagent as claimed in claim 1 comprising a higher fatty acid ester represented by the formula

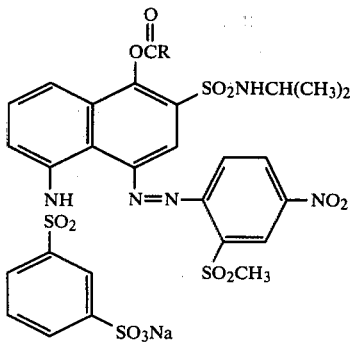

wherein R is n—$C_{11}H_{23}$.

14. A reagent as claimed in claim 1 comprising a higher fatty acid ester represented by the formula

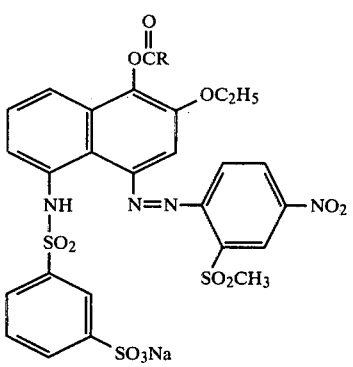

wherein R is n—$C_{11}H_{23}$.

15. A reagent as claimed in claim 1 comprising a higher fatty acid ester represented by the formula

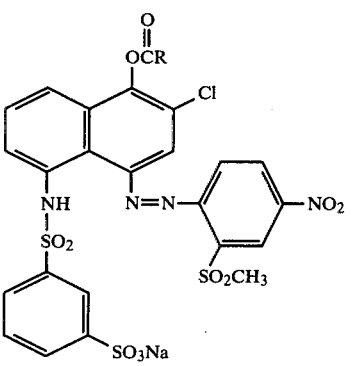

wherein R is n—$C_{11}H_{23}$.

* * * * *